(12) United States Patent
Imamura et al.

(10) Patent No.: US 12,099,926 B2
(45) Date of Patent: Sep. 24, 2024

(54) WATER TREATMENT PLANT AND METHOD FOR OPERATING WATER TREATMENT PLANT

(71) Applicant: Mitsubishi Electric Corporation, Tokyo (JP)

(72) Inventors: Eiji Imamura, Tokyo (JP); Yuki Sato, Tokyo (JP); Wataru Yoshida, Tokyo (JP); Seiji Noda, Tokyo (JP); Yohei Ueno, Tokyo (JP); Nozomu Yasunaga, Tokyo (JP); Go Wakamatsu, Tokyo (JP); Kenta Shimoda, Tokyo (JP); Takushi Kawada, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 822 days.

(21) Appl. No.: 17/259,549

(22) PCT Filed: Jul. 26, 2018

(86) PCT No.: PCT/JP2018/028153
§ 371 (c)(1),
(2) Date: Jan. 12, 2021

(87) PCT Pub. No.: WO2020/021689
PCT Pub. Date: Jan. 30, 2020

(65) Prior Publication Data
US 2021/0133575 A1     May 6, 2021

(51) Int. Cl.
*G06N 3/08*     (2023.01)
*C02F 1/00*     (2023.01)
(Continued)

(52) U.S. Cl.
CPC ............... *G06N 3/08* (2013.01); *C02F 1/008* (2013.01); *G06F 17/18* (2013.01); *G16C 20/70* (2019.02); *C02F 2209/005* (2013.01)

(58) Field of Classification Search
CPC .. G06N 3/08; G06N 3/02; C02F 1/008; C02F 2209/005; G05B 13/027; G05B 2219/25255; G06F 17/18; G16C 20/70
(Continued)

(56) References Cited

U.S. PATENT DOCUMENTS 6,808,630 B2    10/2004   Yang
2018/0082204 A1    3/2018   Iwamasa et al.
(Continued)

FOREIGN PATENT DOCUMENTS

JP     6-304546 A    11/1994
JP     8-52459 A    2/1996
(Continued)

OTHER PUBLICATIONS

Masami et al, English machine translation JP 2008310700A, pp. 1-18 (Year: 2008).*

(Continued)

*Primary Examiner* — Claire A Norris
(74) *Attorney, Agent, or Firm* — XSENSUS LLP

(57) ABSTRACT

A water treatment plant which performs water treatment using a water treatment device includes an imaging device, a processing device, and a control device. The imaging device images a water treatment environment of the water treatment device and outputs image data obtained by imaging. The processing device causes an arithmetic device which performs an arithmetic operation using one or more calculation models generated by machine learning to execute the arithmetic operation employing the image data output from the imaging device as input data of the one or more calculation models. The control device controls the
(Continued)

water treatment device on the basis of output information output from the arithmetic device by executing the arithmetic operation.

12 Claims, 8 Drawing Sheets

(51) Int. Cl.
*G06F 17/18* (2006.01)
*G16C 20/70* (2019.01)

(58) Field of Classification Search
USPC .................................. 210/614, 739; 706/41
See application file for complete search history.

(56) References Cited

U.S. PATENT DOCUMENTS

| | | | |
|---|---|---|---|
| 2021/0171383 A1 | 6/2021 | Hatta et al. | |
| 2021/0263490 A1 | 8/2021 | Ueno et al. | |

FOREIGN PATENT DOCUMENTS

| | | | | |
|---|---|---|---|---|
| JP | 2004-25160 A | | 1/2004 | |
| JP | 2008310700 A | * | 12/2008 | ............... G06N 3/08 |
| JP | 2013-161336 A | | 8/2013 | |
| JP | 2013-185320 A | | 9/2013 | |
| JP | 2018-49390 A | | 3/2018 | |
| WO | 2020/021687 A1 | | 1/2020 | |
| WO | 2020/021688 A1 | | 1/2020 | |

OTHER PUBLICATIONS

Qiao et al, "Recurrent Neural Network-Based Control for wastewater Treatment Process", College of Electronic and Control Engineering, Beijing University of Technology, Beijing, China (Year: 2012).*

International Search Report and Written Opinion mailed on Oct. 2, 2018, received for PCT Application PCT/JP2018/028153, Filed on Jul. 26, 2018, 8 pages including English Translation.

Notice of Reasons for Refusal mailed on Feb. 26, 2019, received for JP Application 2019-504146, 9 pages Including English Translation.

Yoshikura et al., "An Intelligent Operation for Water Treatment Plant by Machine Learning", Research Institute of Electric Engineers, General Incorporated Electric Engineers, Jun. 2, 2018, pp. 5-8.

Office Action issued on Jan. 6, 2022, in corresponding Indian patent Application No. 202127002495, 6 pages.

Chinese Office Action issued Jun. 9, 2022, in corresponding Chinese patent Application No. 201880095731.5.

Office Action issued Jul. 4, 2023 in Korean Patent Application No. 10-2021-7001510, 9 pages.

Office Action issued Mar. 2, 2023 in Korean Patent Application No. 10-2021-7001510, 6 pages.

Korean Office Action dated Sep. 29, 2022, issued in Korean Patent Application No. 10-2021-7001510 with an English machine translation, 12 pp.

Hearing Notice dated Feb. 8, 2024 from the Indian patent office in application No. 202127002495 written in Indian and English languages, 3 pages.

* cited by examiner

| TIME | IMAGE DATA | | | NUMERICAL DATA | | CONTROL TARGET VALUE | |
|---|---|---|---|---|---|---|---|
| t0 | IM1(t0) | IM2(t0) | IM3(t0) | NU1(t0) | ... | RV1(t0) | RV2(t0) |
| t1 | IM1(t1) | IM2(t1) | IM3(t1) | NU1(t1) | ... | RV1(t1) | RV2(t1) |
| t2 | IM1(t2) | IM2(t2) | IM3(t2) | NU1(t2) | ... | RV1(t2) | RV2(t2) |
| : | : | : | : | : | : | : | : |
| tm | IM1(tm) | IM2(tm) | IM3(tm) | NU1(m) | ... | RV1(tm) | RV2(tm) |
| : | : | : | : | : | : | : | : |
| tn | IM1(tn) | IM2(tn) | IM3(tn) | NU1(tn) | ... | RV1(tn) | RV2(tn) |

WATER TREATMENT PLANT AND METHOD FOR OPERATING WATER TREATMENT PLANT

CROSS-REFERENCE TO RELATED APPLICATION

The present application is based on PCT filing PCT/JP2018/028153, filed Jul. 26, 2018, the entire contents of which are incorporated herein by reference.

FIELD

The present invention relates to a water treatment plant which performs treatment of water such as clean water or sewage and a method for operating the water treatment plant.

BACKGROUND

In a water treatment plant, water treatment control is performed while changing a control target value depending on environmental changes. For example, by changing the control target value along with changes in a water treatment environment such as seasonal temperature difference, the flow rate of inflow water, and the quality of inflow water, water treatment control depending on changes in the water treatment environment is performed in the water treatment plant.

The control target value is changed by an operator on the basis of past experience and the like, and specialized expertise is required for performing the change. Patent Literature 1 proposes a technique which uses an artificial intelligent (AI) device for controlling a sewage treatment device so that experience of an operator can be reflected in changing a control target value depending on environmental changes. In such a technique, detection values of multiple sensors which detect the flow rate, temperature, biochemical oxygen demand (BOD), $NH_4+$, and the like of inflow water to the sewage treatment device are input to the AI device, and the sewage treatment device is controlled on the basis of an output of the AI device.

CITATION LIST

Patent Literature

Patent Literature 1: Japanese Patent Application Laid-open No. 2004-25160

SUMMARY

Technical Problem

In such a conventional water treatment plant described above, water treatment control using an AI device is performed with the use of numerical values of the flow rate, temperature, BOD, $NH_4+$ and the like of inflow water as indices. However, such a conventional water treatment plant described above has room for improvement. For example, there may be a case where effective water treatment control cannot be performed in such a conventional water treatment plant described above with respect to a change in a water treatment environment of a water treatment device, the change not appearing in a numerical value detected by a sensor.

The present invention has been made in view of the above, and an object thereof is to obtain a water treatment plant capable of performing more effective water treatment control with respect to a change in a water treatment environment.

Solution to Problem

A water treatment plant according to the present invention is a water treatment plant which performs water treatment using a water treatment device, and includes an imaging device, a processing device, and a control device. The imaging device images a water treatment environment of the water treatment device and outputs image data obtained by imaging. The processing device causes an arithmetic device which performs an arithmetic operation using one or more calculation models generated by machine learning to execute the arithmetic operation employing the image data output from the imaging device as input data of the one or more calculation models. The control device controls the water treatment device on the basis of information output from the arithmetic device by executing the arithmetic operation.

Advantageous Effects of Invention

The present invention achieves an effect that it is possible to provide a water treatment plant capable of performing more effective water treatment control with respect to a change in a water treatment environment.

DESCRIPTION OF EMBODIMENTS

Hereinafter, a water treatment plant and a method for operating the water treatment plant according to an embodiment of the present invention will be described in detail with reference to the drawings. The present invention is not limited to the embodiment.

First Embodiment

Figure 1:
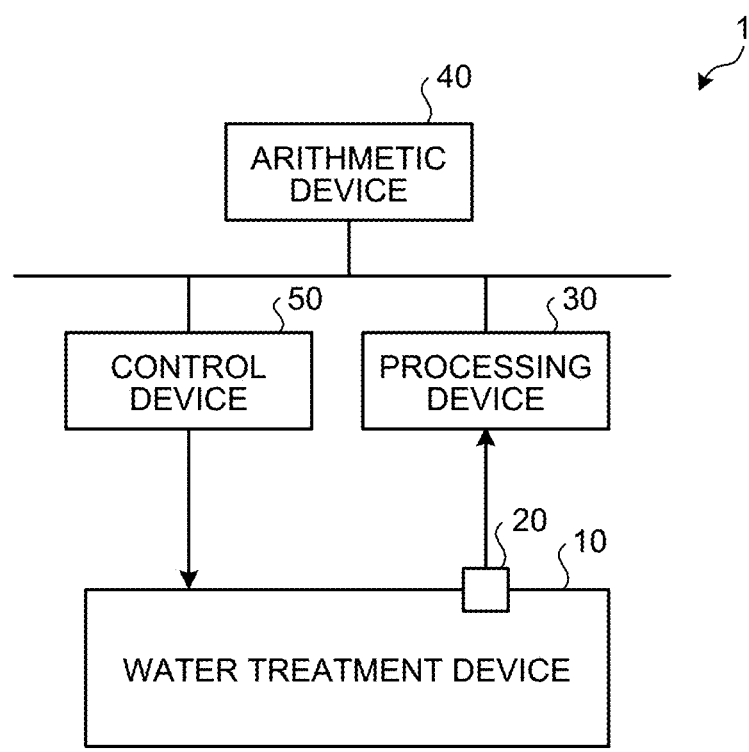
FIG. 1 is a diagram illustrating an outline of a water treatment plant according to a first embodiment.

FIG. 1 is a diagram illustrating an outline of a water treatment plant according to a first embodiment. As illustrated in FIG. 1, a water treatment plant 1 according to the first embodiment includes a water treatment device 10, an imaging device 20, a processing device 30, an arithmetic device 40, and a control device 50. The arithmetic device 40 is an example of an AI device.

The water treatment device 10 is, for example, a device which performs treatment of water such as clean water or sewage, and includes a device to be controlled such as a pump or a blower which controls a water treatment state. An example of the water treatment device 10 is not limited to the device according to the first embodiment which includes the device to be controlled such as a pump or a blower, and a grit chamber, a primary settling basin, a sludge-reducing device, and the like of the water treatment plant may be used.

The control device 50 controls the water treatment device 10. The imaging device 20 images a water treatment environment of the water treatment device 10 and outputs image data of the water treatment environment obtained by imaging. The water treatment environment of the water treatment device 10 includes at least one of a water treatment environment inside the water treatment device 10 and a water treatment environment outside the water treatment device 10. The processing device 30 acquires image data from the imaging device 20.

The processing device 30 causes the arithmetic device 40 to execute an arithmetic operation employing the acquired image data as input data, and acquires a result of the arithmetic operation by the arithmetic device 40 from the arithmetic device 40. The arithmetic device 40 includes a calculation model generated by machine learning. Such a calculation model receives an input of the image data of the imaging device 20, and outputs information on a control target value of the device to be controlled, for example. The control target value is, for example, a target value of the amount of control of the device to be controlled such as a pump or a blower which controls a water treatment state of the water treatment device 10.

The arithmetic device 40 performs an arithmetic operation using the above-described calculation model and employing the image data acquired from the processing device 30 as input data, and outputs information including the result of the arithmetic operation by the arithmetic device 40 to the processing device 30. The processing device 30 outputs the information acquired from the arithmetic device 40 to the control device 50. The control device 50 controls the water treatment device 10 on the basis of the information output from the processing device 30. For example, in a case where the information output from the arithmetic device 40 is the information on the control target value of the device to be controlled, the control device 50 can control the water treatment device 10 by outputting control information including the control target value to the device to be controlled of the water treatment device 10. The arithmetic device 40 is, for example, AI called artificial intelligence or the like, and contributes to estimation of a preferable control target value of the device to be controlled through machine learning based on the input image data.

As described above, in the water treatment plant 1, the water treatment control can be performed using the arithmetic device 40 and employing an image of the water treatment environment of the water treatment device 10 as a new index. Therefore, in the water treatment plant 1, it is possible to perform, with the use of the arithmetic device 40, for example, water treatment control which has been performed by an operator of the water treatment plant 1 on the basis of the image of the water treatment environment of the water treatment device 10 and on the basis of past experience or knowledge of the operator, and to perform effective water treatment control.

In the above-described first embodiment, the example has been described in which the image data of the imaging device 20 is output to the arithmetic device 40 via the processing device 30, and the result of the arithmetic operation by the arithmetic device 40 is output to the processing device 30, thereby controlling the water treatment device 10 by the control device 50. However, the present invention is not limited to the example. For example, modification may be made so that a function of the processing device 30 is incorporated into at least one of the arithmetic device 40 and the control device 50 to omit the processing device 30. In this modification, for example, the processing device 30 which is separate from at least one of the arithmetic device 40 and the control device 50 can be omitted, so that an effect of increasing the degree of freedom in device configuration is achieved.

Figure 2:
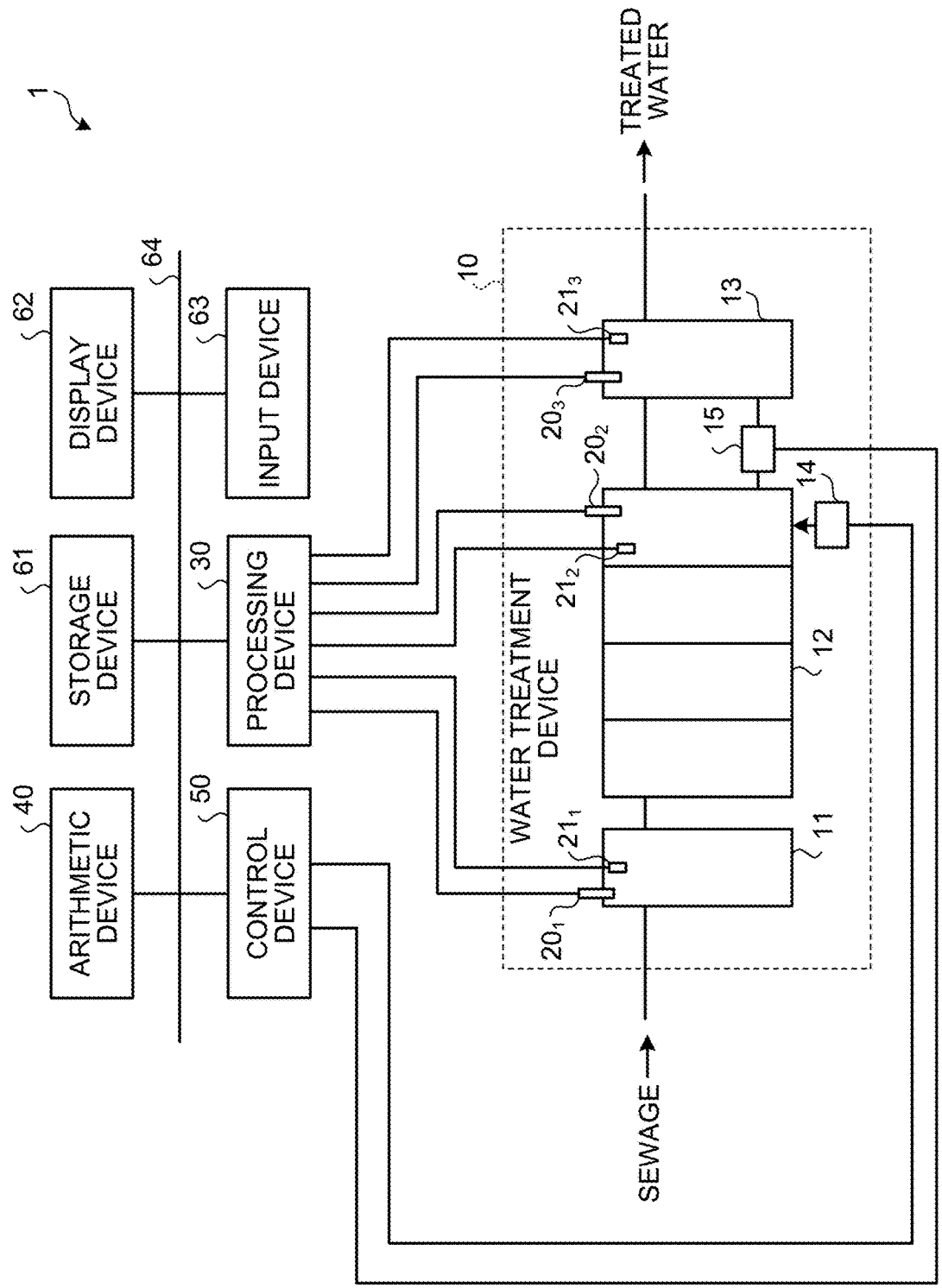
FIG. 2 is a diagram illustrating an example configuration of the water treatment plant according to the first embodiment.

Hereinafter, the water treatment plant 1 according to the first embodiment will be described in detail. FIG. 2 is a diagram illustrating an example configuration of the water treatment plant according to the first embodiment. In the following, sewage treatment will be described as an example of water treatment performed by the water treatment device 10.

As illustrated in FIG. 2, the water treatment plant 1 according to the first embodiment includes the above-described water treatment device 10, imaging devices $20_1$ to $20_3$, sensor groups $21_1$ to $21_3$, the processing device 30, the arithmetic device 40, the control device 50, a storage device 61, a display device 62, and an input device 63. In the following description, the imaging devices $20_1$ to $20_3$ may be referred to as the imaging device 20 when they are indicated without being distinguished from each other, and the sensor groups $21_1$ to $21_3$ may be referred to as the sensor group 21 when they are indicated without being distinguished from each other.

The processing device 30, the arithmetic device 40, the control device 50, the storage device 61, the display device 62, and the input device 63 are communicably connected to each other via a communication network 64. The communication network 64 is, for example, a local area network (LAN), a wide area network (WAN), a bus, or a leased line.

The water treatment device 10 illustrated in FIG. 2 is a sewage treatment device which treats sewage. Such a water treatment device 10 includes a primary settling tank 11 which stores sewage as inflow water from sewerage and the like, and settles a solid substance and the like in the sewage, the solid substance being relatively easy to sink, a treatment tank 12 which aerobically treats supernatant water in the primary settling tank 11, and a final settling tank 13 which separates a liquid mixture containing activated sludge flowing from the treatment tank 12 into supernatant water and activated sludge. The supernatant water in the final settling tank 13 is discharged as treated water from the final settling tank 13.

In the treatment tank 12, the supernatant water which flows therein from the primary settling tank 11 contains organic matter, and the organic matter contained in the supernatant water is treated, for example, by digestion by aerobic microorganisms such as phosphorus accumulating bacteria, nitrifying bacteria, and denitrifying bacteria.

The water treatment device 10 further includes a blower 14 which blows air into the treatment tank 12 to dissolve the air in the liquid mixture containing activated sludge, and a pump 15 which is provided on a pipe which connects the final settling tank 13 and the treatment tank 12, and returns the activated sludge to the treatment tank 12 from the final settling tank 13. Each of the blower 14 and the pump 15 is an example of the device to be controlled described above, and hereinafter, the blower 14 and the pump 15 may be referred to as the device to be controlled when they are indicated without being distinguished from each other.

The multiple imaging devices $20_1$, $20_2$, and $20_3$ image water treatment environments of the water treatment device 10 which are objects to be imaged different from each other. The imaging device $20_1$ images a water treatment environment which is an object to be imaged inside the primary settling tank 11. The object to be imaged inside the primary settling tank 11 is, for example, a state of water, a state of bubbles, or a state of settlings in the primary settling tank 11.

The imaging device $20_2$ images a water treatment environment which is an object to be imaged inside the treatment tank 12. The object to be imaged inside the treatment tank 12 is, for example, a state of activated sludge or a state of water in the treatment tank 12. The state of activated sludge includes, for example, the amount or distribution of the activated sludge. The state of activated sludge may be, for example, the amount of each microorganism.

The imaging device $20_3$ images a water treatment environment which is an object to be imaged inside the final settling tank 13. The object to be imaged inside the final settling tank 13 is, for example, a state of supernatant water or a state of settlings in the final settling tank 13. In the following description, the primary settling tank 11, the treatment tank 12, and the final settling tank 13 may be referred to as a tank when they are indicated without being distinguished from each other. The objects to be imaged which are imaged by the imaging device 20 are not limited to the above-described examples, and the imaging device 20 can also image a state of an inner wall of the tank, a state of surroundings of the tank, or the like as the object to be imaged. Although the imaging devices $20_1$, $20_2$, and $20_3$ illustrated in FIG. 2 image the state or environment inside the water treatment device 10 as the water treatment environment of the water treatment device 10, an imaging device may be provided which images a state or environment outside the water treatment device 10 illustrated in FIG. 2.

The imaging device 20 is, for example, a digital camera, or a digital microscope. The imaging device 20 may be, for example, a digital camera for a microscope. In such a case, when the operator of the water treatment plant 1 places water in the tank or the like under the microscope, the imaging device 20 can image a microscopic image thereof. The number of imaging devices 20 is not limited to three, and may be two or less, or four or more. Hereinafter, the operator of the water treatment plant 1 will be simply referred to as the operator.

The multiple sensor groups $21_1$ to $21_3$ detect various characteristics indicating the water treatment environment of the water treatment device 10. For example, the sensor group $21_1$ detects an inflow water characteristic which is a characteristic of inflow water to the primary settling tank 11.

The sensor group $21_2$ detects an intra-treatment-tank characteristic which indicates a state of the treatment tank 12. The sensor group $21_3$ detects a treated water characteristic which is a characteristic of treated water discharged from the final settling tank 13.

Figure 3:
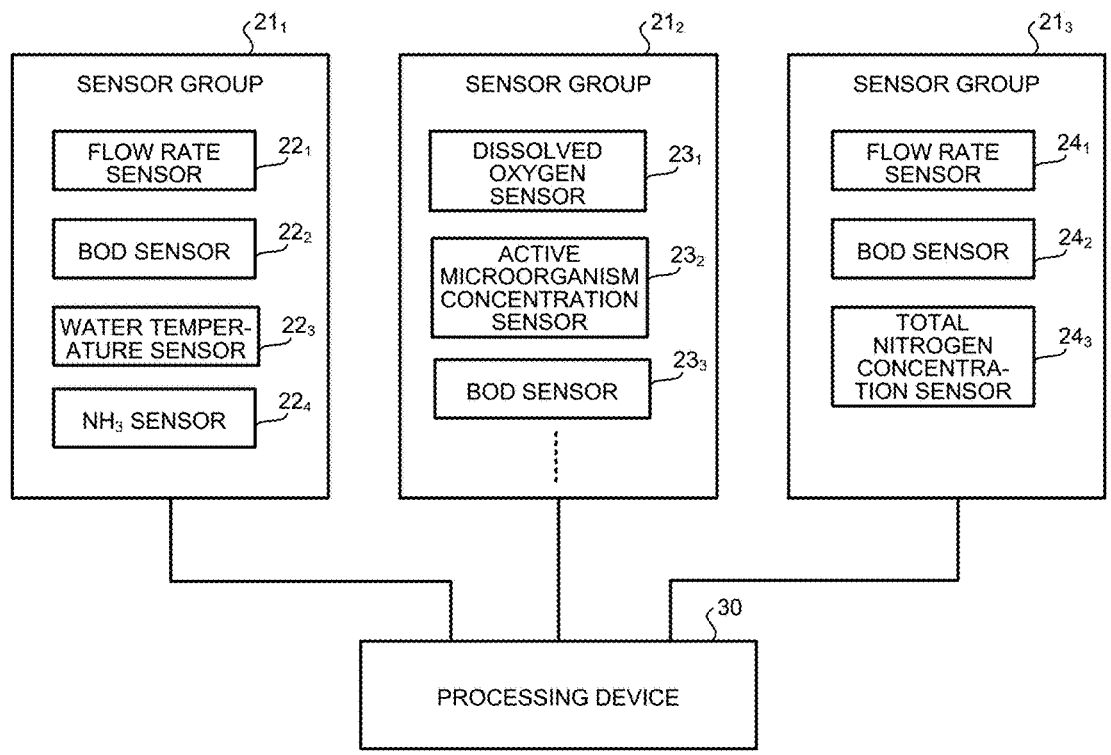
FIG. 3 is a diagram illustrating example configurations of multiple sensor groups according to the first embodiment.

FIG. 3 is a diagram illustrating example configurations of the multiple sensor groups according to the first embodiment. As illustrated in FIG. 3, the sensor group $21_1$ includes a flow rate sensor $22_1$ which detects the inflow amount of inflow water, a BOD sensor $22_2$ which detects the BOD of the inflow water, a water temperature sensor $22_3$ which detects the temperature of the inflow water, and an $NH_3$ sensor $22_4$ which detects the $NH_3$ concentration in the inflow water. The sensor group $21_1$ may include a sensor for detecting the $NH_4^+$ or ammoniacal nitrogen concentration in the inflow water instead of or in addition to the $NH_3$ sensor $22_4$.

The sensor group $21_2$ includes a dissolved oxygen sensor $23_1$ which detects the amount of dissolved oxygen in the treatment tank 12, an active microorganism concentration sensor $23_2$ which detects the active microorganisms concentration in the treatment tank 12, and a BOD sensor $23_3$ which detects the BOD in the treatment tank 12. In addition, the sensor group $21_2$ further includes multiple sensors each of which detects one of the ammoniacal nitrogen concentration, a nitrate nitrogen concentration, a total nitrogen concentration, a phosphate phosphorus concentration, and a total phosphorus concentration.

The sensor group $21_3$ includes a flow rate sensor $24_1$ which detects the outflow amount of treated water, a BOD sensor $24_2$ which detects the BOD of the treated water, and a total nitrogen concentration sensor $24_3$ which detects the total nitrogen concentration in the treated water.

The sensor groups $21_1$ to $21_3$ may include a sensor which detects an object other than the above-described objects to be detected, or may not include a part of the multiple sensors described above. Hereinafter, data of numerical values detected by each sensor in the sensor groups $21_1$ to $21_3$ will be referred to as numerical data. In addition, image data and numerical data may be referred to as detection data when they are indicated without being distinguished from each other.

The processing device 30 acquires image data output from the imaging device 20 and numerical data output from the sensor group 21, and stores the acquired image data and numerical data in the storage device 61. The processing device 30 causes the arithmetic device 40 to execute an arithmetic operation employing data selected between the image data output from the imaging device 20 and the numerical data output from the sensor group 21 as input data, and acquires information including a result of the arithmetic operation by the arithmetic device 40. The processing device 30 transmits the information output from the arithmetic device 40 to the control device 50, and stores the information output from the arithmetic device 40 in the storage device 61.

In addition, the processing device 30 can display the image data output from the imaging device 20 on the display device 62. The operator can determine, for example, on the basis of an image of the inside of the tank displayed on the display device 62, whether there is a sign of a future unfavorable intra-tank state in the water treatment device 10. The term "future" here means, for example, several hours ahead or one or more days ahead.

The future unfavorable intra-tank state includes, for example, a state where the removal of organic matter becomes insufficient, a state where the removal of nitrogen becomes insufficient, and a state where a filtration membrane (not illustrated) becomes easily clogged. In addition, the sign of the future unfavorable intra-tank state includes, for example, a state where the number of microorganisms which inhibit water treatment is increasing, or a state where the distribution of microorganisms which perform water treatment exhibits a specific distribution. In the water treatment plant 1 according to the first embodiment, it is possible to determine the sign of the future unfavorable intra-tank state described above on the basis of the image data of the imaging device 20. Therefore, it is possible to contribute to improvement in diversification and accuracy of grounds for determination of signs, as compared with determination of signs using numerical data only. Hereinafter, the sign of the future unfavorable intra-tank state may be simply referred to as the sign.

In a case where the operator determines that the image of the inside of the tank displayed on the display device 62 indicates the above-described sign, by operating the input device 63, the operator can generate or update a calculation model included in the arithmetic device 40 employing, as learning data, image data at a time when an environmental change indicating the sign occurs.

Figure 4:
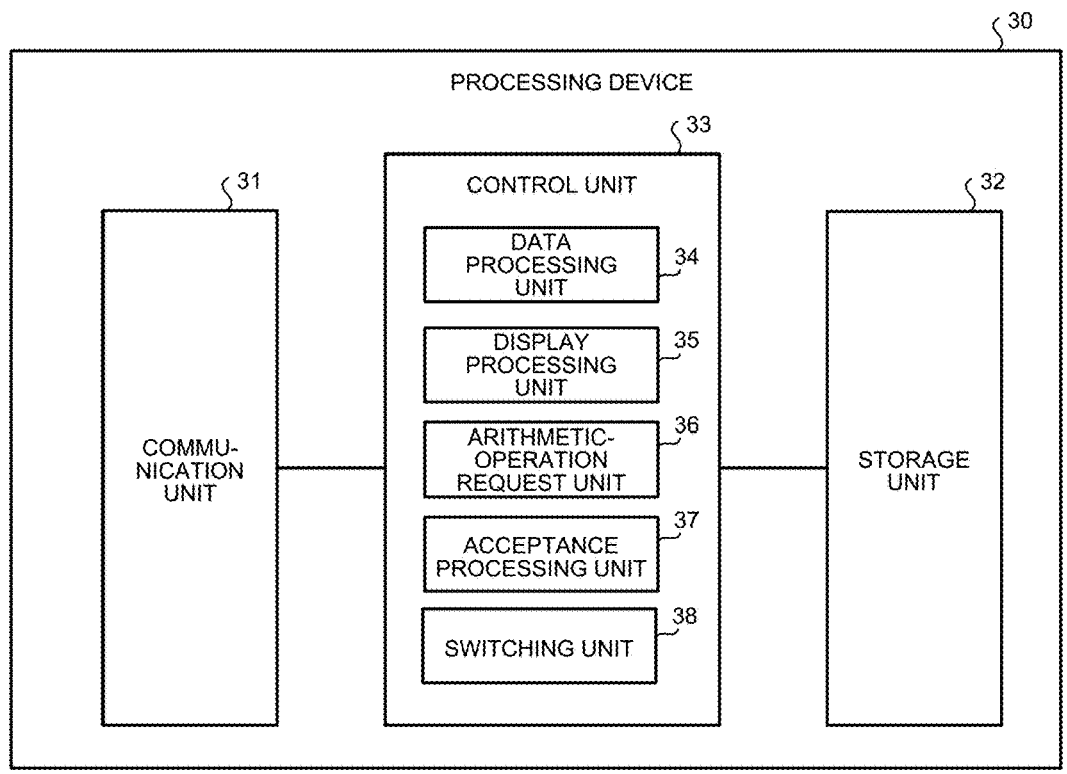
FIG. 4 is a diagram illustrating an example configuration of a processing device according to the first embodiment.

FIG. 4 is a diagram illustrating an example configuration of the processing device according to the first embodiment. As illustrated in FIG. 4, the processing device 30 includes a communication unit 31, a storage unit 32, and a control unit 33. The communication unit 31 is connected to the communication network 64. The control unit 33 can transmit and receive data to and from each of the arithmetic device 40, the control device 50, the storage device 61, the display device 62, and the input device 63 via the communication unit 31 and the communication network 64.

The control unit 33 includes a data processing unit 34, a display processing unit 35, an arithmetic-operation request unit 36, an acceptance processing unit 37, and a switching unit 38. The data processing unit 34 repeatedly acquires image data output from the imaging device 20 and numerical data output from the sensor group 21, and stores the acquired image data and numerical data in the storage device 61.

The data processing unit 34 stores the image data acquired from each imaging device 20 in the storage device 61 in association with time. In addition, the data processing unit 34 stores the numerical data acquired from each sensor in the storage device 61 in association with time. Furthermore, the data processing unit 34 acquires information output from the arithmetic device 40, outputs the acquired information to the control device 50, and stores the acquired information in the storage device 61.

Figures 5, 6:
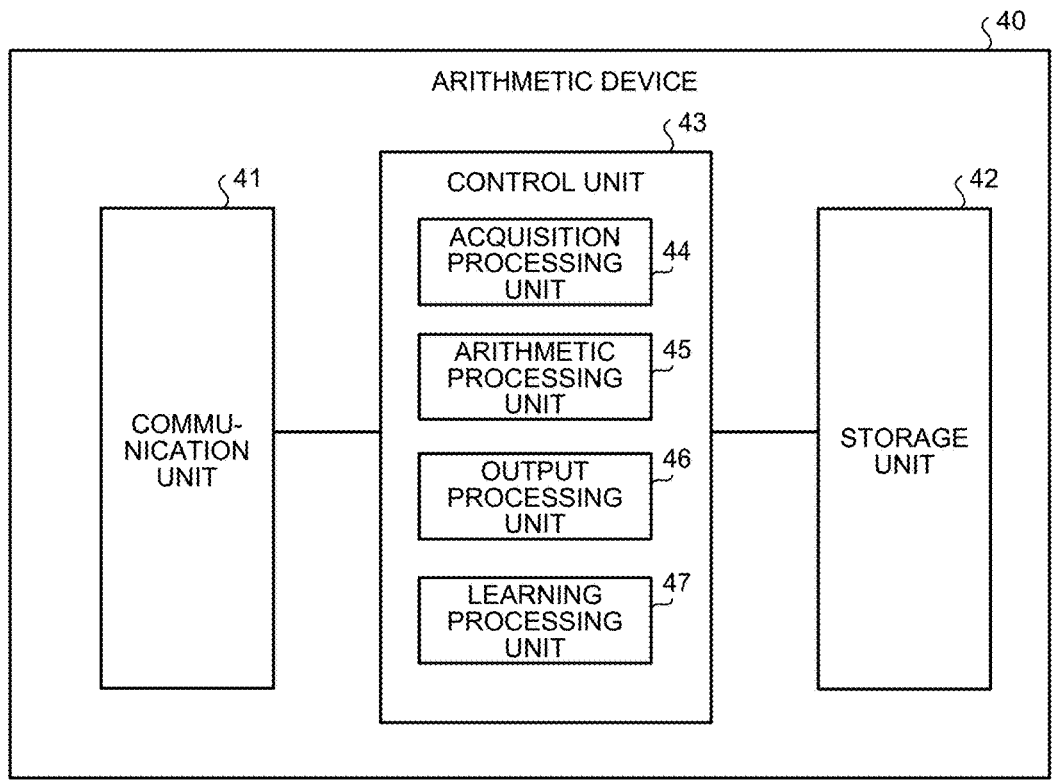
FIG. 5 is a diagram illustrating an example of a data table stored in a storage device according to the first embodiment.
FIG. 6 is a diagram illustrating an example configuration of an arithmetic device according to the first embodiment.

FIG. 5 is a diagram illustrating an example of a data table stored in the storage device according to the first embodiment. The data table illustrated in FIG. 5 includes image data, numerical data, and control target values for each time. In FIG. 5, image data IM1($t0$), IM1($t1$), . . . , IM1($tm$), . . . , and IM1($tn$) are image data of the imaging device $20_1$. In addition, image data IM2($t0$), IM2($t1$), . . . , IM2($tm$), . . . , and IM2($tn$) are image data of the imaging device $20_2$.

Furthermore, image data IM3($t0$), IM3($t1$), . . . , IM3($tm$), . . . , and IM3($tn$) are image data of the imaging device $20_3$. Note that m and n are natural numbers, and n>m is established. Although FIG. 5 illustrates numerical data of one sensor, i.e. NU1($t0$), NU1($t1$), . . . , NU1($tm$), . . . , and NU1($tn$) only, the data table also includes numerical data of the rest of sensors.

In addition, the data table illustrated in FIG. 5 includes information on the control target value of each device to be controlled output to the control device 50 by the processing device 30 at each time. In FIG. 5, control target values RV1($t0$), RV1($t1$), . . . , RV1($tm$), . . . , and RV1($tn$) are control target values of the blower 14. In addition, control target values RV2($t0$), RV2($t1$), . . . , RV2($tm$), . . . , and RV2($tn$) are control target values of the pump 15.

Returning to FIG. 4, the description of the control unit 33 will be continued. The display processing unit 35 displays the image data and the numerical data acquired by the data processing unit 34 on the display device 62. In addition, the display processing unit 35 can acquire, from the storage device 61, the information input by the operator operating the input device 63, and can display the acquired information on the display device 62.

The arithmetic-operation request unit 36 outputs, to the arithmetic device 40 via the communication network 64, data necessary for inputting a calculation model which satisfies a selection condition described later, out of the image data and the numerical data acquired by the data processing unit 34.

For example, in a case where the calculation model which satisfies the selection condition is a calculation model for an image, the arithmetic-operation request unit 36 outputs the image data acquired by the data processing unit 34 to the arithmetic device 40. In addition, in a case where the calculation model which satisfies the selection condition is a calculation model for a sensor, the arithmetic-operation request unit 36 outputs the numerical data acquired by the data processing unit 34 to the arithmetic device 40.

Furthermore, in a case where the calculation models which satisfy the selection conditions are the calculation model for an image and the calculation model for a sensor, the arithmetic-operation request unit 36 outputs the image data and the numerical data acquired by the data processing unit 34 to the arithmetic device 40. It is also possible for the arithmetic-operation request unit 36 to acquire the data necessary for inputting the calculation model which satisfies the selection condition from the storage device 61 and to output the acquired data to the arithmetic device 40.

The arithmetic-operation request unit 36 outputs detection data to the arithmetic device 40, thereby causing the arithmetic device 40 to execute an arithmetic operation employing the detection data as input data. The data processing unit 34 acquires information indicating a result of the arithmetic operation output from the arithmetic device 40, and outputs the acquired information to the control device 50. The information output from the arithmetic device 40 includes, for example, control information including the control target value of the device to be controlled, and the control device 50 controls the water treatment device 10 by controlling the device to be controlled provided in the water treatment device 10 on the basis of the information output from the processing device 30.

The acceptance processing unit 37 accepts selection of image data for generating and updating multiple calculation models included in the arithmetic device 40 on the basis of an operation on the input device 63 performed by the operator. The arithmetic-operation request unit 36 acquires image data, the selection of which has been accepted by the acceptance processing unit 37, from the storage device 61. In addition, the arithmetic-operation request unit 36 acquires, from the storage device 61, information on the control target value of each device to be controlled associated with time when the selected image data was acquired.

The arithmetic-operation request unit 36 transmits learning data in which the selected image data and object-to-be-controlled data are associated with each other, to the arithmetic device 40 via the communication network 64. In the learning data, the object-to-be-controlled data associated with the selected image data is data including the control target values acquired from the storage device 61 and the type of each device to be controlled. For example, in a case where the selected image data are image data IM1(*tm*), IM2(*tm*), and IM3(*tm*) at a time tm illustrated in FIG. 5, the object-to-be-controlled data includes control target values RV1(*tm*) and RV2(*tm*) illustrated in FIG. 5.

The acceptance processing unit 37 can also accept information on a period for selecting time-series image data stored in the storage device 61, on the basis of the operation on the input device 63 performed by the operator. For example, the acceptance processing unit 37 can accept an operation on the input device 63 for selecting image data for the past year.

The arithmetic-operation request unit 36 acquires, from the storage device 61, time-series image data output from the imaging device 20 during the period accepted by the acceptance processing unit 37. In addition, the arithmetic-operation request unit 36 acquires, from the storage device 61, data of time-series control target values set in each device to be controlled during the period accepted by the acceptance processing unit 37. The arithmetic-operation request unit 36 transmits learning data including the acquired time-series image data and data of time-series control target values to the arithmetic device 40 via the communication network 64.

In addition, as will be described later, in a case where the calculation model for an image is, for example, a recurrent neural network which outputs information on a score indicating the degree whether an environmental change indicating the above-described sign has occurred, the operator can select correct data and incorrect data. For example, the operator can select, as the correct data, image data imaged by the imaging device 20 in a state where there is the above-described sign in the water treatment device 10. In addition, the operator can select, as the incorrect data, for example, image data imaged by the imaging device 20 at a time when there is no above-described sign.

The switching unit 38 can operate in a manual switching mode in which the selection condition is changed on the basis of the operation on the input device 63 performed by the operator. For example, in a case where the acceptance processing unit 37 accepts a selection condition switching operation performed by the operator when the operation mode of the switching unit 38 is the manual switching mode, the switching unit 38 changes the selection condition set in the storage unit 32.

In addition, the switching unit 38 can also operate in an automatic switching mode in which the selection condition is automatically changed. For example, in a case where the operation mode of the switching unit 38 is the automatic switching mode and the selection condition is set at the calculation model for a sensor, the switching unit 38 determines whether a first switching condition is satisfied. If it is determined that the first switching condition is satisfied, the switching unit 38 changes the selection condition set in the storage unit 32 from the calculation model for a sensor to the calculation model for an image. As a result, the calculation model used in the arithmetic device 40 is changed to the calculation model for an image.

For example, in a case where a numerical value indicated by numerical data of one or more specific sensors included in the multiple sensor groups 21 is outside a preset range continuously for a preset period of time or longer, the switching unit 38 can determine that the first switching condition is satisfied. The first switching condition is not limited to conditions of the detection results of the sensors, and may be a condition of, for example, time of day, season, weather, or any other condition.

In addition, in a case where the operation mode of the switching unit 38 is the automatic switching mode and the calculation model for an image is set as the selection condition, the switching unit 38 determines whether a second switching condition is satisfied. If it is determined that the second switching condition is satisfied, the switching unit 38 changes the selection condition set in the storage unit 32 from the calculation model for an image to the calculation model for a sensor. As a result, the calculation model used in the arithmetic device 40 is changed to the calculation model for a sensor.

For example, in a case where a numerical value indicated by numerical data of one or more specific sensors included in the multiple sensor groups 21 is inside a preset range continuously for a preset period of time or longer, the switching unit 38 can determine that the second switching condition is satisfied. The second switching condition is not limited to conditions of the detection results of the sensors, and may be a condition of, for example, time of day, season, weather, or any other condition.

The operation mode of the switching unit 38 can be changed on the basis of an operation performed by the operator. In addition, the switching unit 38 can change the calculation models alternately between the calculation model for a sensor and the calculation model for an image. For example, the switching unit 38 can set the calculation model for a sensor in a first period T1, and can set the calculation model for an image in a second period T2 which comes alternately with the first period T1. In such a case, it is possible to mainly perform water treatment control with numerical values while performing water treatment control with images by making the second period T2 shorter than the first period T1.

Next, the arithmetic device 40 will be described. FIG. 6 is a diagram illustrating an example configuration of the arithmetic device according to the first embodiment. As illustrated in FIG. 6, the arithmetic device 40 includes a communication unit 41, a storage unit 42, and a control unit 43.

The communication unit 41 is connected to the communication network 64. The control unit 43 can transmit and receive data to and from each of the imaging device 20, the processing device 30, the control device 50, the storage device 61, and the input device 63 via the communication unit 41 and the communication network 64.

The storage unit 42 stores multiple calculation models. The multiple calculation models stored in the storage unit 42 include the above-described calculation model for an image and calculation model for a sensor.

The calculation model for an image is, for example, a convolutional neural network which receives inputs of multiple image data output from multiple imaging devices 20 and outputs control target values of multiple devices to be controlled. With the use of the convolutional neural network, as compared to a case of using a general neural network, learning of image data is efficiently performed by sharing weights, which makes it possible to acquire highly accurate results. In consideration of the variety of system architecture, the calculation model for an image may be a neural network other than the convolutional neural network.

The calculation model for a sensor is, for example, a neural network which receives inputs of multiple numerical data output from multiple sensors provided in the multiple sensor groups $21_1$ to $21_3$ and outputs control target values of multiple devices to be controlled. The calculation model for a sensor is a neural network suitable for an arithmetic operation of numerical data, unlike the convolutional neural network which is a calculation model for an image. In addition, for example, the calculation model for a sensor may be a calculation model generated by a learning algorithm such as linear regression or logistic regression. The calculation model for a sensor may be a convolutional neural network because the degree of freedom in device configuration is increased.

The control unit 43 includes an acquisition processing unit 44, an arithmetic processing unit 45, an output processing unit 46, and a learning processing unit 47. The acquisition processing unit 44 acquires detection data from the processing device 30 via the communication network 64 and the communication unit 41. The detection data from the processing device 30 includes image data, numerical data, or image data and numerical data, as described above.

The arithmetic processing unit 45 reads, from the storage unit 42, a calculation model corresponding to the detection data acquired by the acquisition processing unit 44, inputs the detection data to the read calculation model to perform an arithmetic operation using the calculation model, thereby acquiring an output of the calculation model. For example, in a case where the detection data acquired by the acquisition processing unit 44 is image data, the arithmetic processing unit 45 inputs the image data to the calculation model for an image to perform an arithmetic operation using the calculation model for an image, and acquires an output of the calculation model for an image.

In addition, in a case where the detection data acquired by the acquisition processing unit 44 is numerical data, the arithmetic processing unit 45 inputs the numerical data to the calculation model for a sensor to perform an arithmetic operation using the calculation model for a sensor, and acquires an output of the calculation model for a sensor.

In addition, in a case where the detection data acquired by the acquisition processing unit 44 includes image data and numerical data, the arithmetic processing unit 45 uses both the calculation model for an image and the calculation model for a sensor. That is, the arithmetic processing unit 45 inputs the image data out of the image data and the numerical data to the calculation model for an image to perform an arithmetic operation using the calculation model for an image, and acquires information output from the calculation model for an image. Furthermore, the arithmetic processing unit 45 inputs the numerical data out of the image data and the numerical data to the calculation model for a sensor to perform an arithmetic operation using the calculation model for a sensor, and acquires information output from the calculation model for a sensor.

The output processing unit 46 outputs, as the output information of the arithmetic device 40, information acquired by the arithmetic operation using each calculation model in the arithmetic processing unit 45 to the processing device 30 from the communication unit 41. The information output from each calculation model is information on the control target values of the multiple devices to be controlled described above.

In the case where the detection data acquired by the acquisition processing unit 44 includes image data and numerical data, the output processing unit 46 can select one of information output from the calculation model for a sensor and information output from the calculation model for an image to output the selected information to the processing device 30 from the communication unit 41.

For example, in a case where a difference between the control target value output from the calculation model for an image and the control target value output from the calculation model for a sensor is a preset value or larger, the output processing unit 46 selects the control target value output from the calculation model for an image and outputs the control target value to the processing device 30. In addition, in a case where the difference between the control target value output from the calculation model for an image and the control target value output from the calculation model for a sensor is smaller than the preset value, the output processing unit 46 selects the control target value output from the calculation model for a sensor and outputs the control target value to the processing device 30.

In the case where the detection data acquired by the acquisition processing unit 44 includes image data and numerical data, the arithmetic processing unit 45 can perform, for each device to be controlled, an arithmetic operation of an average value of the control target value output from the calculation model for a sensor and the control target value output from the calculation model for an image. The output processing unit 46 can output, as output information, control information including the average value of the control target values for each device to be controlled obtained by the arithmetic operation by the arithmetic processing unit 45.

The calculation model for an image may include a recurrent neural network in addition to the convolutional neural network described above. In such a case, the arithmetic processing unit 45 inputs time-series image data imaged by the imaging device 20 to the recurrent neural network, and acquires, from the recurrent neural network, data of an image predicted to be imaged by the imaging device 20 after the elapse of a time Ta. The time Ta is, for example, 12 hours or longer. Then, the arithmetic processing unit 45 inputs the data of the image predicted to be imaged by the imaging device 20 after the elapse of the time Ta to the convolutional neural network, and acquires information output from the convolutional neural network.

In addition, the calculation model for an image may include the recurrent neural network only. Such a recurrent neural network receives an input of, for example, time-series image data imaged by the imaging device 20, and outputs information on a score indicating the degree whether an environmental change indicating the above-described sign has occurred. Such a recurrent neural network is stored for each type of sign in the storage unit 42. In the storage unit 42, control information, which is information in which the type and the control target value of each device to be controlled are associated with each other, is stored for each type of sign. Such control information can be stored in the storage unit 42 by the operator operating the input device 63, for example.

The arithmetic processing unit 45 can input the time-series image data imaged by the imaging device 20 to the recurrent neural network for each type of sign to acquire information on a score output from each recurrent neural network. The arithmetic processing unit 45 acquires, from the storage unit 42, control information including the type and the control target value of the device to be controlled associated with the type of sign of which score is equal to or higher than a threshold. In addition, in a case where there are multiple types of sign of which scores are equal to or higher than the threshold, the arithmetic processing unit 45 acquires, from the storage unit 42, control information including the type and the control target value of the device to be controlled associated with the type of sign of which score is highest. The arithmetic processing unit 45 outputs the acquired control information including the type and the control target value of the device to be controlled to the processing device 30 from the communication unit 41 as output information of the arithmetic device 40.

The learning processing unit 47 can generate and update the above-described calculation model for an image on the basis of the learning data output from the processing device 30. The learning processing unit 47 stores the generated or updated calculation model for an image in the storage unit 42.

For example, in a case where the calculation model for an image includes a convolutional neural network, the learning processing unit 47 can generate or update the calculation model for an image by optimizing the convolutional neural network on the basis of the image data and the object-to-be-controlled data included in the learning data.

In a case where the calculation model for an image includes the recurrent neural network, the learning processing unit 47 can generate or update the calculation model for an image by optimizing the recurrent neural network on the basis of the learning data including the time-series image data.

The neural network in the arithmetic device 40 is an artificial neural network. The artificial neural network is a calculation model in which perceptrons are hierarchically arranged, each of the perceptrons obtaining a weighted sum of input signals, applying a non-linear function called an activation function thereto, and outputting a result of the application. The output out of the perceptron can be expressed by the following equation (1), in which the input is expressed by $X=(x1, x2, \ldots, xn)$, the weight is expressed by $W=(w1, w2, \ldots, wn)$, the activation function is expressed by $f(.)$, and the element-wise product of vectors is expressed by $*$.

$$\text{out}=f(X*W) \tag{1}$$

In the convolutional neural network, perceptrons each receive a two-dimensional signal corresponding to an image as an input, calculate a weighted sum of the inputs, and pass results of the calculation to the next layer. As the activation function, a sigmoid function or a rectified linear unit (ReLU) function is used.

The above-described perceptrons are hierarchically arranged in the artificial neural network, and an identification result is calculated by processing an input signal in each layer. In a final layer, for example, if the type of task in the artificial neural network is a regression task, an output of the activation function is used as it is as an output of the task, and if the type of task is a classification task, a softmax function is applied regarding the final layer, and a result of the application is used as an output of the task.

In a case of the convolutional neural network, an artificial network is configured as a map of two-dimensional signals. It can be considered that each of the two-dimensional signals corresponds to the perceptron. With respect to a feature map of the previous layer, the weighted sum is calculated and the activation function is applied, and a result thereof is output.

The above-described process is called a convolution operation in the convolutional neural network, and in addition thereto, a pooling layer for performing a pooling process may be inserted in each layer. The pooling layer performs downsampling by performing an averaging operation or a maximum operation on a feature map.

Learning by such an artificial neural network is performed by back propagation, and for example, a known stochastic gradient descent method is used. The back propagation is a framework in which an output error of the artificial neural network is propagated from the final layer to previous layers in sequence to update weights.

Next, the control device 50 illustrated in FIG. 2 will be described. The control device 50 can control the water treatment device 10 by controlling the blower 14, the pump 15, and the like. For example, by controlling the blower 14 to adjust the amount of air blown into a liquid mixture containing activated sludge, the control device 50 can control the concentration of dissolved oxygen in the liquid mixture containing activated sludge. In addition, by controlling the pump 15, the control device 50 adjusts the flow rate of activated sludge returned to the treatment tank 12 from the final settling tank 13.

Figure 7:
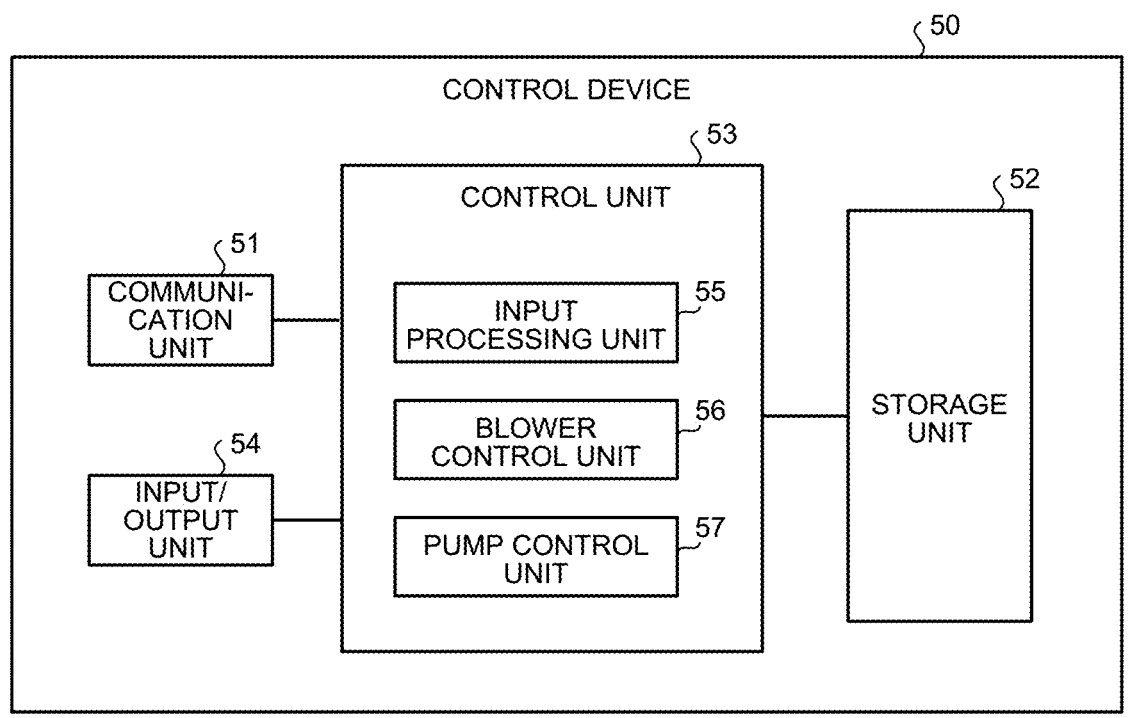
FIG. 7 is a diagram illustrating an example configuration of a control device according to the first embodiment.

FIG. 7 is a diagram illustrating an example configuration of the control device according to the first embodiment. As illustrated in FIG. 7, the control device 50 includes a communication unit 51, a storage unit 52, a control unit 53, and an input/output unit 54. The communication unit 51 is connected to the communication network 64. The control unit 53 can transmit and receive data to and from the processing device 30 via the communication unit 51 and the communication network 64.

The control unit 53 includes an input processing unit 55, a blower control unit 56, and a pump control unit 57. The input processing unit 55 acquires control information output from the processing device 30 via the communication unit 51, and stores the acquired control information in the storage unit 52. The control information stored in the storage unit 52 includes a control target value of the blower 14 and a control target value of the pump 15.

The blower control unit 56 reads the control target value of the blower 14 stored in the storage unit 52. In addition, the blower control unit 56 acquires numerical data indicating the amount of dissolved oxygen detected by the dissolved oxygen sensor $23_1$ from the storage device 61 or the dissolved oxygen sensor $23_1$. The blower control unit 56 generates a control signal by proportional integral (PI) control or proportional integral differential (PID) control on the basis of the control target value of the blower 14 and the acquired amount of dissolved oxygen. The blower control unit 56 outputs the generated control signal to the blower 14 from the input/output unit 54. The blower 14 adjusts the amount of air blown into the treatment tank 12 on the basis of the control signal output from the input/output unit 54 of the control device 50.

The pump control unit 57 reads the control target value of the pump 15 stored in the storage unit 52. In addition, the pump control unit 57 acquires, from a sensor (not illustrated) via the input/output unit 54, numerical data indicating the flow rate of the activated sludge to the treatment tank 12 from the final settling tank 13. The pump control unit 57 generates a control signal by PI control or PID control on the basis of the control target value of the pump 15 and the acquired flow rate of the activated sludge. The pump control unit 57 outputs the generated control signal to the pump 15 from the input/output unit 54. The pump 15 adjusts the flow rate of the activated sludge to the treatment tank 12 from the final settling tank 13 on the basis of the control signal output from the input/output unit 54 of the control device 50.

Figure 8:
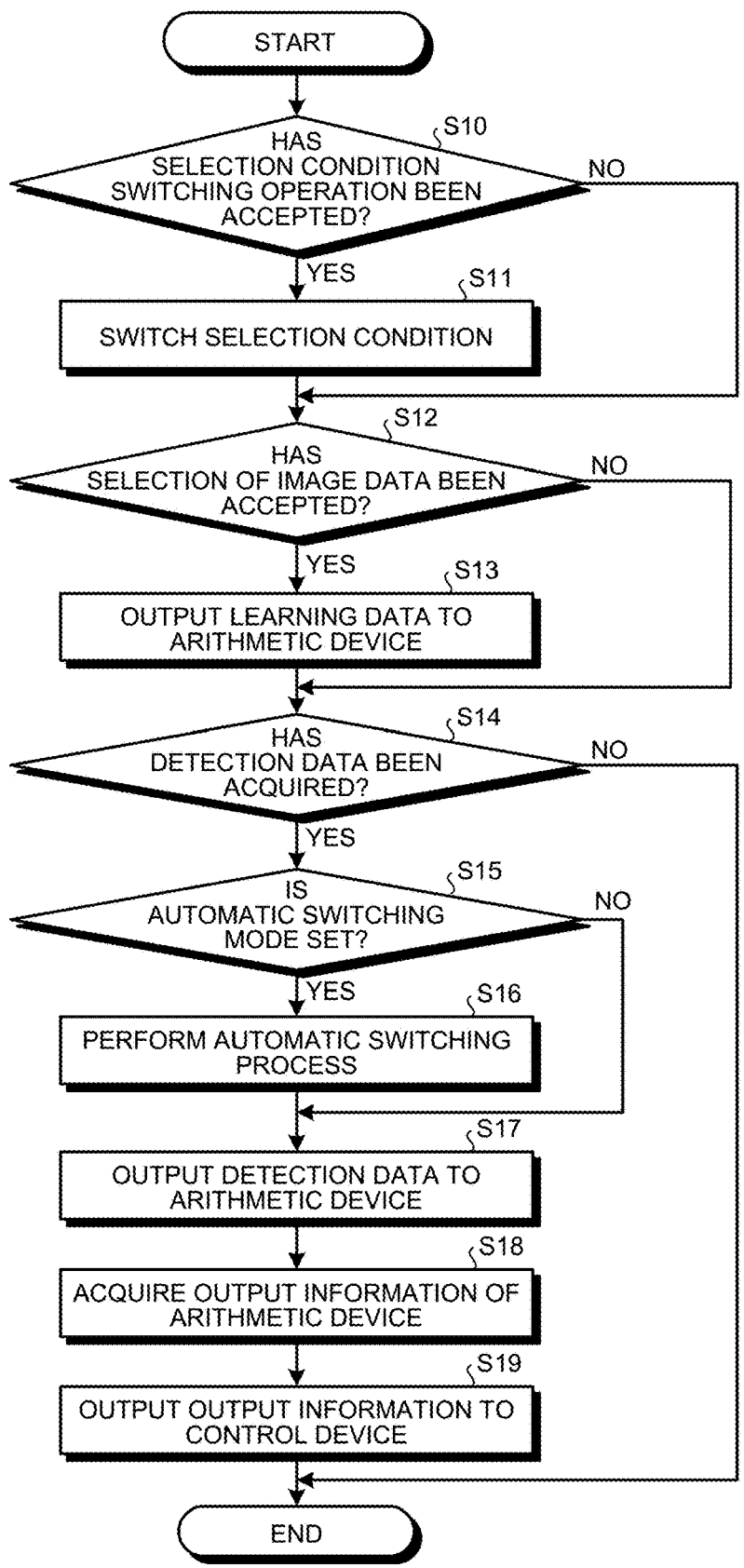
FIG. 8 is a flowchart illustrating an example of a series of processes of the processing device according to the first embodiment.

Next, an operation of the water treatment plant 1 will be described with reference to a flowchart. FIG. 8 is a flowchart illustrating an example of a series of processes of the processing device according to the first embodiment, and the series of processes is repeatedly executed by the control unit 33 of the processing device 30.

As illustrated in FIG. 8, the control unit 33 of the processing device 30 determines whether a selection condition switching operation has been accepted from the operator (step S10). If it is determined that the selection condition switching operation has been accepted (step S10: Yes), the control unit 33 switches the selection condition by changing the selection condition stored in the storage unit 32 to a selection condition depending on the switching operation (step S11).

When the process of step S11 ends, or if it is determined that the selection condition switching operation has not been accepted (step S10: No), the control unit 33 determines whether selection of image data has been accepted from the operator (step S12). If it is determined that the selection of image data has been accepted (step S12: Yes), the control unit 33 outputs learning data including the selected image data to the arithmetic device 40 (step S13).

When the process of step S13 ends, or if it is determined that the selection of the image data has not been accepted (step S12: No), the control unit 33 determines whether the detection data has been acquired (step S14). If it is determined that the detection data has been acquired (step S14: Yes), the control unit 33 determines whether the operation mode is the automatic switching mode (step S15).

If it is determined that the operation mode is the automatic switching mode (step S15: Yes), the control unit 33 performs an automatic switching process (step S16). In step S16, when the control unit 33 determines that the first switching condition is satisfied in a state where the calculation model for a sensor is set as the selection condition, the control unit 33 sets the calculation model for an image as the selection condition. In addition, when the control unit 33 determines that the second switching condition is satisfied in a state where the calculation model for an image is set as the selection condition, the control unit 33 sets the calculation model for a sensor as the selection condition.

When the process of step S16 ends, or if it is determined that the operation mode is not the automatic switching mode (step S15: No), the control unit 33 acquires detection data corresponding to the selection condition from the storage device 61, and outputs the acquired detection data to the arithmetic device 40 (step S17). In step S17, for example, in a case where the set selection condition is the calculation model for an image, the detection data corresponding to the selection condition is image data. In addition, in a case where the set selection condition is the calculation model for a sensor, the detection data corresponding to the selection condition is numerical data.

Next, the control unit 33 acquires output information output from the arithmetic device 40 in response to step S17 (step S18), and outputs the acquired output information to the control device 50 (step S19). Such output information includes the control information as described above. When the process of step S19 ends, or if it is determined that the detection data has not been acquired (step S14: No), the control unit 33 ends the processes illustrated in FIG. 8.

Figure 9:
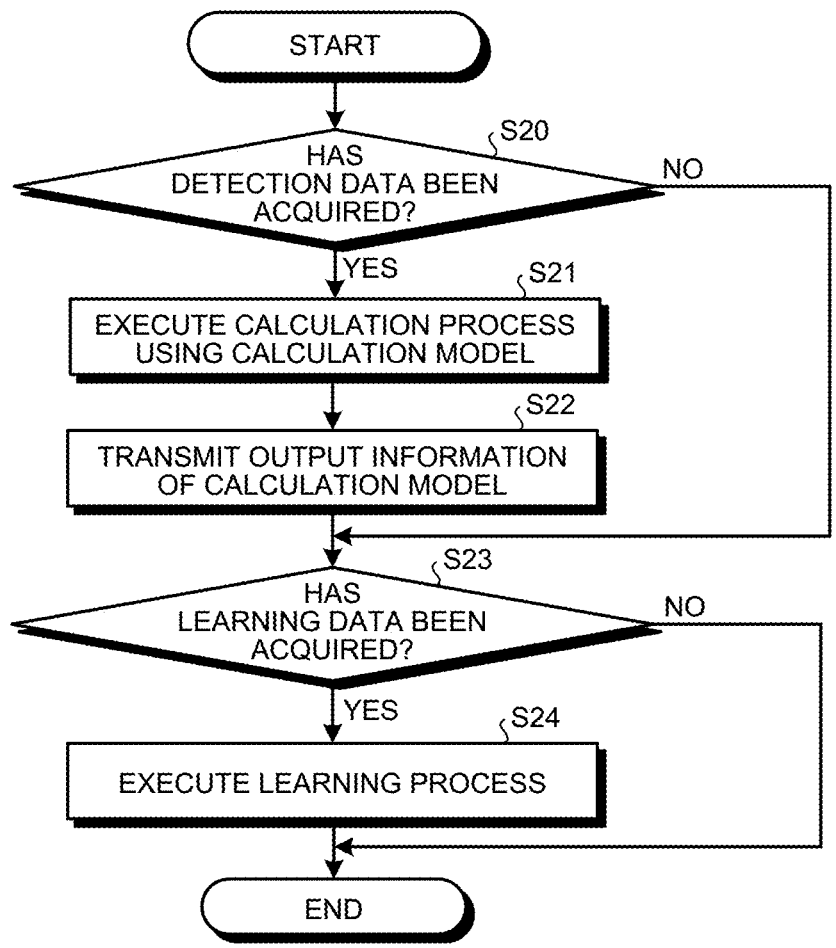
FIG. 9 is a flowchart illustrating an example of a series of processes of the arithmetic device according to the first embodiment.

FIG. 9 is a flowchart illustrating an example of a series of processes of the arithmetic device according to the first embodiment, and the series of processes is repeatedly executed by the control unit 43 of the arithmetic device 40.

As illustrated in FIG. 9, the control unit 43 of the arithmetic device 40 determines whether the detection data has been acquired from the processing device 30 (step S20). If it is determined that the detection data has been acquired (step S20: Yes), the control unit 43 executes an arithmetic process using a calculation model and employing the acquired detection data as an input of the calculation model (step S21), and transmits output information of the calculation model to the processing device 30 (step S22).

When the process of step S22 ends, or if it is determined that the detection data has not been acquired (step S20: No), the control unit 43 determines whether the learning data has been acquired from the processing device 30 (step S23). If it is determined that the learning data has been acquired from the processing device 30 (step S23: Yes), the control unit 43 executes a learning process of the calculation model using the learning data (step S24).

When the process of step S24 ends, or if it is determined that the learning data has not been acquired (step S23: No), the control unit 43 ends the processes illustrated in FIG. 9.

Figure 10:
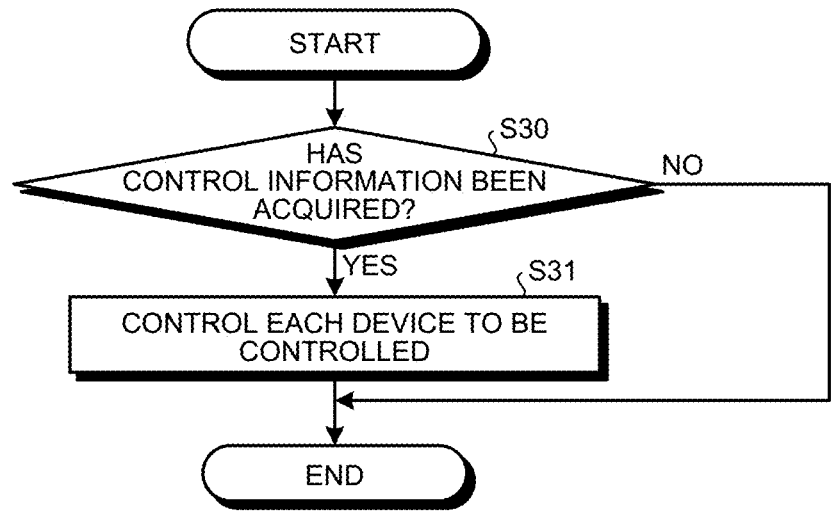
FIG. 10 is a flowchart illustrating an example of a series of processes of the control device according to the first embodiment.

FIG. 10 is a flowchart illustrating an example of a series of processes of the control device according to the first embodiment, and the series of processes is repeatedly executed by the control unit 53 of the control device 50.

As illustrated in FIG. 10, the control unit 53 of the control device 50 determines whether the control information has been acquired from the processing device 30 (step S30). If it is determined that the control information has been acquired (step S30: Yes), the control unit 53 controls each device to be controlled on the basis of the acquired control information (step S31). When the process of step S31 ends, or if it is determined that the control information has not been acquired (step S30: No), the control unit 53 ends the processes illustrated in FIG. 10.

Figure 11:
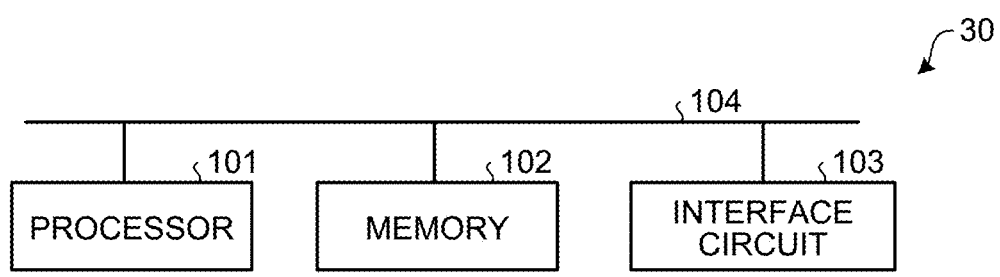
FIG. 11 is a diagram illustrating an example of a hardware configuration of the processing device according to the first embodiment.

FIG. 11 is a diagram illustrating an example of a hardware configuration of the processing device according to the first embodiment. As illustrated in FIG. 11, the processing device 30 includes a computer including a processor 101, a memory 102, and an interface circuit 103.

The processor 101, the memory 102, and the interface circuit 103 can transmit and receive data to and from each other via a bus 104. The communication unit 31 is realized by the interface circuit 103. The storage unit 32 is realized by the memory 102. The processor 101 executes functions of the data processing unit 34, the display processing unit 35, the arithmetic-operation request unit 36, the acceptance processing unit 37, and the switching unit 38 by reading and executing programs stored in the memory 102. The processor 101 is an example of a processing circuit, and includes one or more of a central processing unit (CPU), a digital signal processor (DSP), and system large scale integration (LSI).

The memory 102 includes one or more of a random access memory (RAM), a read only memory (ROM), a flash memory, and an erasable programmable read only memory (EPROM). In addition, the memory 102 includes a recording medium in which the above-described programs readable by the computer are recorded. Such a recording medium includes one or more of a non-volatile or volatile semiconductor memory, a magnetic disk, a flexible memory, an optical disk, a compact disc, and a DVD.

In a case where the control unit 33 of the processing device 30 is realized by dedicated hardware, the control unit 33 is, for example, a single circuit, a composite circuit, a programmed processor, a parallel programmed processor, an application specific integrated circuit (ASIC), a field programmable gate array (FPGA), or a combination thereof.

The arithmetic device 40 also includes a hardware configuration similar to the hardware configuration illustrated in FIG. 11. The communication unit 41 is realized by the interface circuit 103. The storage unit 42 is realized by the memory 102. The processor 101 executes functions of the acquisition processing unit 44, the arithmetic processing unit 45, the output processing unit 46, and the learning processing unit 47 by reading and executing the programs stored in the memory 102. In a case where the control unit 43 is realized by dedicated hardware, the control unit 43 is a single circuit, a composite circuit, a programmed processor, a parallel programmed processor, an ASIC, an FPGA, or a combination thereof.

The control device 50 also includes a hardware configuration similar to the hardware configuration illustrated in FIG. 11. The communication unit 51 and the input/output unit 54 are realized by the interface circuit 103. The storage unit 52 is realized by the memory 102. The processor 101 executes functions of the input processing unit 55, the blower control unit 56, and the pump control unit 57 by reading and executing programs stored in the memory 102. In a case where the control unit 53 is realized by dedicated hardware, the control unit 53 is a single circuit, a composite circuit, a programmed processor, a parallel programmed processor, an ASIC, an FPGA, or a combination thereof.

In the example described above, the information output from the arithmetic device 40 is output to the control device 50 from the processing device 30, but a configuration may be employed in which the information output from the arithmetic device 40 is directly input to the control device 50 without the processing device 30.

In a case where the calculation model for an image includes the recurrent neural network, it is possible to output, to the processing device 30 for each type of sign, information on a sign score which is a score indicating the degree whether there is the sign of the future unfavorable intra-tank state in the water treatment device 10. In such a case, the display processing unit 35 of the processing device 30 can display the acquired sign score for each type of sign on the display device 62.

In the above-described example, the calculation model which employs image data only as input data has been described as an example of the calculation model for an image, but the calculation model for an image may be a calculation model which employs, in addition to image data, numerical data or other data as input data.

Although the convolutional neural network which receives inputs of multiple image data and outputs multiple control target values has been described above as an example of the calculation model for an image, the calculation model for an image is not limited to the example described above. For example, the convolutional neural network can be provided for each control target value as the calculation model for an image. The convolutional neural network can be provided for each imaging device 20 as the calculation model for an image. In addition, the convolutional neural network can be provided for each imaging device 20 and each device to be controlled as the calculation model for an image.

In the above-described example, in a case where the calculation model for an image includes the recurrent neural network only, the control information, which is information in which the type and the control target value of each device to be controlled are associated with each other, is stored for each type of sign, but there is not limitation to such an example. For example, the arithmetic device 40 can also generate or update the recurrent neural network by performing machine learning on the basis of the time-series image data and the time-series control target values stored in the storage device 61. In such a case, the recurrent neural network outputs the control target values from the time-series image data. As a result, effective water treatment can be performed, for example, even in a case where there is a sign in the water treatment plant 1, the sign being one of multiple signs of the future unfavorable intra-tank state and being not yet recognized by the operator.

In the above-described example, the blower 14 and the pump 15 have been described as examples of the device to be controlled which is controlled by using the arithmetic device 40, but the device to be controlled which is controlled by using the arithmetic device 40 may include devices other than the blower 14 and the pump 15.

As described above, the water treatment plant 1 according to the first embodiment includes the water treatment device 10 which performs water treatment, the imaging device 20, the processing device 30, the arithmetic device 40, and the control device 50. The imaging device 20 images a water treatment environment of the water treatment device 10 and outputs image data obtained by imaging. The processing device 30 causes the arithmetic device 40 which performs an arithmetic operation using one or more calculation models generated by machine learning to execute the arithmetic operation employing the image data output from the imaging device 20 as input data of the one or more calculation models. The control device 50 controls the water treatment device 10 on the basis of output information output from the arithmetic device 40 by executing the arithmetic operation. Therefore, in the water treatment plant 1, it is possible to perform, with the use of the arithmetic device 40, for example, water treatment control which has been performed by the operator of the water treatment plant 1 on the basis of an image of the water treatment environment of the water treatment device 10 and on the basis of past experience or knowledge of the operator. Therefore, more effective water treatment control can be performed with respect to a change in the water treatment environment.

In addition, the one or more calculation models include a convolutional neural network employing image data as input data. The processing device 30 causes the arithmetic device 40 to execute an arithmetic operation using the convolutional neural network. The convolutional neural network is an example of the calculation model for an image. As described above, by preparing the convolutional neural network employing image data as input data and causing the arithmetic device 40 to execute the arithmetic operation using the convolutional neural network on the image data output from the imaging device 20, the water treatment device 10 can be accurately controlled.

The water treatment plant 1 includes a sensor which detects a characteristic indicating the water treatment environment of the water treatment device 10 and outputs numerical data of the detected characteristic. The arithmetic device 40 includes a neural network for a sensor which employs numerical data output from the sensor as input data. The neural network for a sensor is an example of the calculation model for a sensor described above. The processing device 30 causes the arithmetic device 40 to execute an arithmetic operation using the neural network for a sensor. As described above, by detecting the characteristic indicating the water treatment environment of the water treatment device 10 with a sensor 2, outputting numerical data of the detected characteristic from the sensor 2, preparing the neural network for a sensor which employs the numerical data output from the sensor 2 as input data, and causing the arithmetic device 40 to execute the arithmetic operation using the neural network for a sensor on the numerical data output from the sensor 2, it is possible to control the water treatment device 10 using a detection result of the sensor.

The processing device 30 includes the switching unit 38 which performs switching between the use of the convolutional neural network and the use of the neural network for a sensor to cause the arithmetic device 40 to execute the arithmetic operation. As a result, the water treatment device 10 can be accurately controlled, for example, by performing switching between the water treatment control using the image imaged by the imaging device 20 and the water treatment control using the detection result by the sensor depending on the situation.

In addition, the processing device 30 includes the acceptance processing unit 37 which accepts selection of one or more image data from multiple image data imaged by the imaging device 20. The arithmetic device 40 executes machine learning of one or more calculation models on the basis of the one or more image data accepted by the acceptance processing unit 37. As a result, for example, the calculation models included in the arithmetic device 40 can be updated, and the water treatment device 10 can be accurately controlled.

The control device 50 controls each device to be controlled provided in the water treatment device 10 by proportional-integral control or proportional-integral-derivative control. As a result, the water treatment device 10 can be accurately controlled.

The water treatment device 10 includes the devices to be controlled which are objects to be controlled by the control device 50. The processing device 30 causes the arithmetic device 40 to execute an arithmetic operation to generate control target values RV1 and RV2 of the devices to be controlled. The control device 50 controls the water treatment device 10 employing the control target values RV1 and RV2 caused to be generated by the processing device 30 as output information. As a result, the devices to be controlled provided in the water treatment device 10 can be accurately controlled.

The configurations described in the embodiment above are merely examples of the content of the present invention and can be combined with other known technology and part thereof can be omitted or modified without departing from the gist of the present invention.

REFERENCE SIGNS LIST 1 water treatment plant; 10 water treatment device; 11 primary settling tank; 12 treatment tank; 13 final settling tank; 14 blower; 15 pump; 20, $20_1$, $20_2$, $20_3$ imaging device; 21, $21_1$, $21_2$, $21_3$ sensor group; $22_1$ flow rate sensor; $22_2$ BOD sensor; $22_3$ water temperature sensor; $22_4$ $NH_3$ sensor; $23_1$ dissolved oxygen sensor; $23_2$ active microorganism concentration sensor; $23_3$ BOD sensor; $24_1$ flow rate sensor; $24_2$ BOD sensor; $24_3$ total nitrogen concentration sensor; 30 processing device; 31, 41, 51 communication unit; 32, 42, 52 storage unit; 33, 43, 53 control unit; 34 data processing unit; 35 display processing unit; 36 arithmetic-operation request unit; 37 acceptance processing unit; 38 switching unit; 40 arithmetic device; 44 acquisition processing unit; 45 arithmetic processing unit; 46 output processing unit; 47 learning processing unit; 50 control device; 54 input/output unit; 55 input processing unit; 56 blower control unit; 57 pump control unit; 61 storage device; 62 display device; 63 input device; 64 communication network.

The invention claimed is:

1. A water treatment plant that performs water treatment using a water treatment device, the water treatment plant comprising:
a monitor to image a water treatment environment of the water treatment device and to output image data obtained by imaging;
a sensor to detect a characteristic that indicates a state of a water treatment environment of the water treatment device and to output numerical data of the detected characteristic;
an arithmetic circuitry configured to perform an arithmetic operation using two or more calculation models including a first neural network and a second neural network to execute the arithmetic operation employing the image data output from the imaging device as input data of the first neural network and to execute the arithmetic operation employing the numerical data output from the sensor as input data of the second neural network, the first neural network being a convolutional neural network, and the second neural network being different from the first neural network;
processing circuitry to cause the arithmetic circuitry to perform the arithmetic operation; and
a control circuitry to control the water treatment device on a basis of output information output from the arithmetic circuitry by executing the arithmetic operation, wherein
the processing circuitry
includes a switching circuitry configured to perform switching between use of the first neural network and use of the second neural network to cause the arithmetic circuitry to execute the arithmetic operation.

2. The water treatment plant according to claim 1, wherein
the processing circuitry
includes an acceptance processing circuitry to accept selection of one or more image data among a plurality of image data imaged by the imaging device, and
the arithmetic circuitry
is configured to execute machine learning of the two or more calculation models on a basis of the one or more image data accepted by the acceptance processing circuitry.

3. The water treatment plant according to claim 1, wherein the control circuitry is configured to control a device to be controlled provided in the water treatment device by proportional-integral control or proportional-integral-derivative control.

4. The water treatment plant according to claim 1, wherein the arithmetic circuitry is configured to be trained by machine learning.

5. The water treatment plant according to claim 1, wherein the water treatment device includes a device to be controlled by the control circuitry,
the processing circuitry is configured to cause the arithmetic circuitry to execute the arithmetic operation to generate a control target value of the device to be controlled, and
the control circuitry controls the water treatment device using the control target value caused to be generated by the processing circuitry as the output information.

6. The water treatment plant according to claim 1, wherein the switching circuitry is configured to perform the switching between the use of one of the first neural network and the second neural network and another one of the first neural network and the second neural network based on a selection condition.

7. The water treatment plan according to claim 6, wherein the switching circuitry is configured to set the selection condition based on at least one of a manual operation by an operator, a determination that the numerical data output from the sensor is outside a preset range continuously for a present period of time or longer, a time of day, a season, and a weather condition.

8. A method for operating a water treatment plant that performs water treatment using a water treatment device, the method comprising:
- imaging a water treatment environment of the water treatment device and outputting image data obtained by imaging;
- detecting a characteristic that indicates a state of a water treatment environment of the water treatment device by a sensor and outputting numerical data of the detected characteristic;
- causing an arithmetic circuitry that performs an arithmetic operation using two or more calculation models including a first neural network and a second neural network to execute the arithmetic operation employing the image data output as input data of the first neural network and to execute the arithmetic operation employing the numerical data output from the sensor as input data of the second neural network, the first neural network being a convolutional neural network, and the second neural network being different from the first neural network;
- controlling the water treatment device on a basis of output information output from the arithmetic circuitry by executing the arithmetic operation; and
- performing switching between use of the first neural network and use of the second neural network to cause the arithmetic circuitry to execute the arithmetic operation.

9. The method for operating a water treatment plant according to claim 8, comprising:
- accepting selection of one or more image data from a plurality of the image data imaged; and
- executing machine learning of the two or more calculation models on a basis of the one or more image data selected.

10. The method for operating a water treatment plant according to claim 8, wherein
in controlling the water treatment device,
a device to be controlled provided in the water treatment device is controlled by proportional-integral control or proportional-integral-derivative control.

11. The method for operating a water treatment plant according to claim 8, comprising:
training the arithmetic circuitry with machine learning.

12. The method for operating a water treatment plant according to claim 8, wherein
the water treatment device includes a device to be controlled, and
the method comprises:
- causing a control target value of the device to be controlled to be generated as output information output from the arithmetic circuitry by executing the arithmetic operation; and
- controlling the water treatment device employing the control target value generated as the output information.

* * * * *